(12) United States Patent
Piskun et al.

(10) Patent No.: US 7,753,901 B2
(45) Date of Patent: Jul. 13, 2010

(54) LAPAROSCOPIC INSTRUMENT AND CANNULA ASSEMBLY AND RELATED SURGICAL METHOD

(75) Inventors: Gregory Piskun, Morganville, NJ (US); Anatoly Konik, Haifa, IL (US); Dan Rottenberg, Haifa, IL (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 10/895,546

(22) Filed: Jul. 21, 2004

(65) Prior Publication Data

US 2006/0020241 A1   Jan. 26, 2006

(51) Int. Cl.
*A61M 1/00* (2006.01)
*A61M 5/178* (2006.01)
*A61F 11/00* (2006.01)

(52) U.S. Cl. .................. 604/539; 604/164.01; 606/108

(58) Field of Classification Search ................ 604/539, 604/523, 528, 533, 174–5, 164.01, 164.04, 604/64.07, 164.09, 165.01, 165.02, 165.04, 604/164.07; 606/108
See application file for complete search history.

(56) References Cited

U.S. PATENT DOCUMENTS

| | | | |
|---|---|---|---|
| 2,669,991 A | | 2/1954 | Curutchet |
| 4,112,932 A | * | 9/1978 | Chiulli ........................ 604/264 |
| 4,644,951 A | | 2/1987 | Bays |
| 4,863,430 A | | 9/1989 | Klyce et al. |
| 5,026,366 A | * | 6/1991 | Leckrone ........................ 606/7 |
| 5,241,968 A | | 9/1993 | Slater |
| 5,242,409 A | | 9/1993 | Buelna |
| 5,269,772 A | * | 12/1993 | Wilk ........................ 604/284 |
| 5,330,486 A | | 7/1994 | Wilk |
| 5,334,143 A | * | 8/1994 | Carroll ........................ 604/514 |
| 5,375,588 A | * | 12/1994 | Yoon ........................ 600/114 |
| 5,395,327 A | | 3/1995 | Lundquist et al. |
| 5,395,367 A | * | 3/1995 | Wilk ........................ 606/1 |
| 5,480,410 A | | 1/1996 | Cuschieri et al. |
| 5,540,648 A | * | 7/1996 | Yoon ........................ 600/114 |
| 5,549,563 A | | 8/1996 | Kronner |
| 5,549,637 A | | 8/1996 | Crainich |
| 5,571,115 A | | 11/1996 | Nicholas |
| 5,571,137 A | | 11/1996 | Marlow et al. |
| 5,575,799 A | | 11/1996 | Bolanos et al. |
| 5,578,048 A | | 11/1996 | Pasqualucci et al. |
| 5,651,771 A | * | 7/1997 | Tangherlini et al. ......... 604/158 |
| 5,672,168 A | | 9/1997 | de la Torre et al. |
| 5,725,536 A | | 3/1998 | Oberlin et al. |
| 5,782,859 A | | 7/1998 | Nicholas et al. |
| 5,810,712 A | * | 9/1998 | Dunn ........................ 600/114 |
| 5,857,461 A | * | 1/1999 | Levitsky et al. ......... 128/207.14 |
| 5,860,995 A | | 1/1999 | Berkelaar |
| 5,931,832 A | | 8/1999 | Jensen |
| 5,964,781 A | | 10/1999 | Mollenauer et al. |
| 6,042,573 A | | 3/2000 | Lucey |
| 6,217,555 B1 | * | 4/2001 | Hart et al. .............. 604/167.01 |
| 6,217,590 B1 | | 4/2001 | Levinson |
| 6,238,373 B1 | | 5/2001 | de la Torre et al. |

(Continued)

*Primary Examiner*—Kevin C Sirmons
*Assistant Examiner*—Andrew M Gilbert

(57) ABSTRACT

A laparoscopic port assembly includes a cannula unit including three cannulas each extending at an acute angle relative to a base. The cannulas are flexible for receiving respective angulated laparoscopic instruments. The cannula unit is rotatingly received in a port holder for rotation about a longitudinal axis of the holder, the holder being disposable in an opening in a patient's skin.

24 Claims, 8 Drawing Sheets

U.S. PATENT DOCUMENTS

| | | | |
|---|---|---|---|
| 6,319,246 B1 * | 11/2001 | de la Torre et al. .............. 606/1 |
| 6,440,061 B1 * | 8/2002 | Wenner et al. .............. 600/114 |
| 6,454,783 B1 * | 9/2002 | Piskun ...................... 606/185 |
| 6,464,686 B1 * | 10/2002 | O'Hara et al. .............. 604/539 |
| 6,488,620 B1 * | 12/2002 | Segermark et al. .......... 600/208 |
| 6,551,270 B1 * | 4/2003 | Bimbo et al. ............ 604/93.01 |
| 6,551,276 B1 * | 4/2003 | Mann et al. ................. 604/131 |
| 6,669,674 B1 * | 12/2003 | Macoviak et al. .......... 604/264 |
| 6,706,050 B1 | 3/2004 | Giannadakis |
| 6,878,110 B2 | 4/2005 | Yang et al. |
| 6,902,569 B2 * | 6/2005 | Parmer et al. ............... 606/108 |
| 7,235,084 B2 * | 6/2007 | Skakoon et al. ............. 606/130 |
| 2003/0036748 A1 | 2/2003 | Cooper et al. |
| 2003/0114832 A1 | 6/2003 | Kohler et al. |
| 2004/0167543 A1 * | 8/2004 | Mazzocchi et al. .......... 606/130 |
| 2008/0255519 A1 * | 10/2008 | Piskun et al. ............... 604/174 |

* cited by examiner

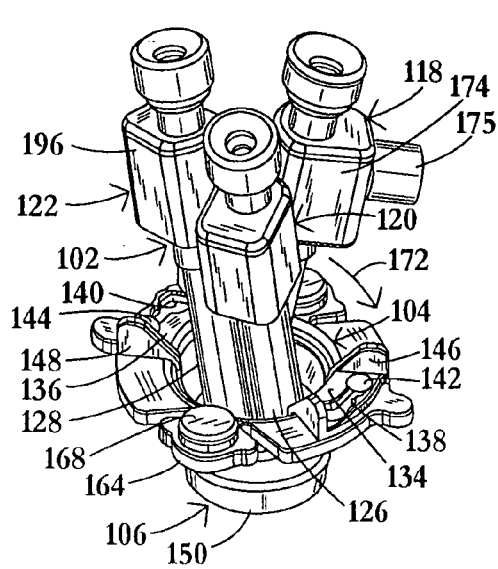
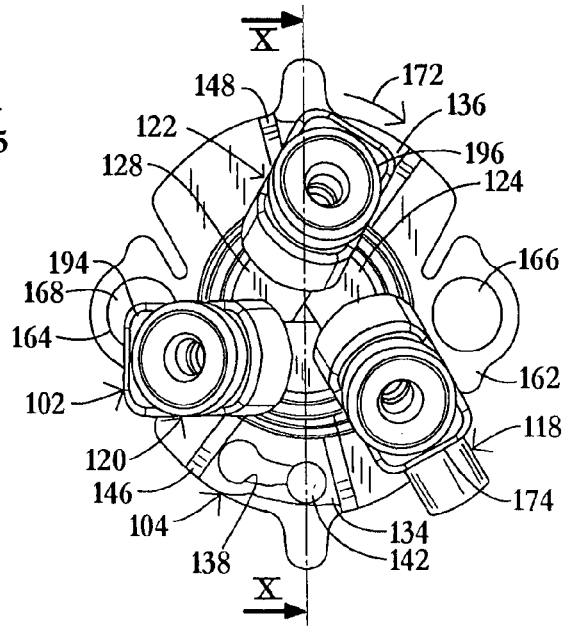
FIG. 8   FIG. 9
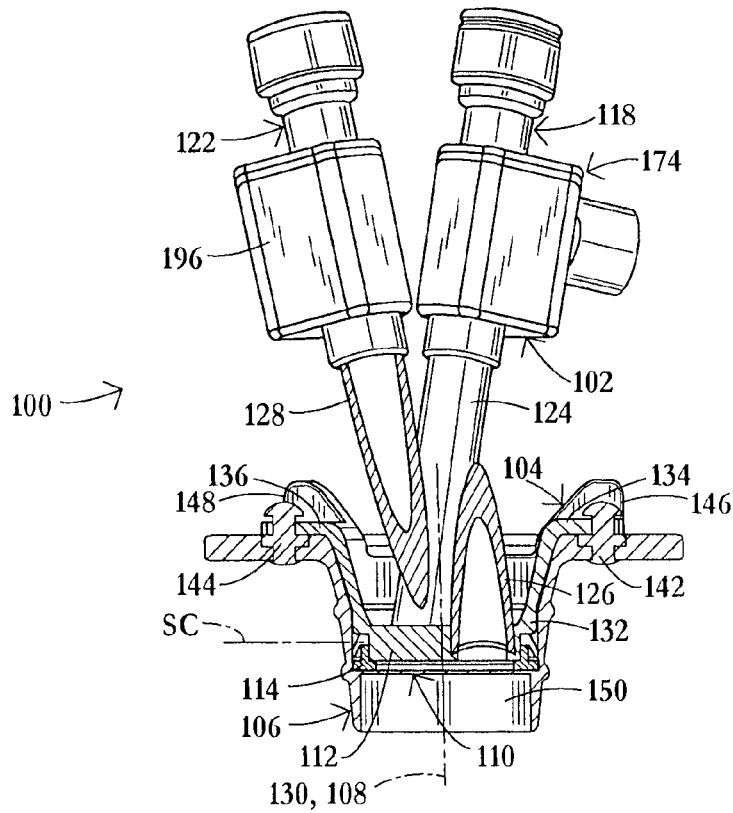
FIG. 10

LAPAROSCOPIC INSTRUMENT AND CANNULA ASSEMBLY AND RELATED SURGICAL METHOD

FIELD OF THE INVENTION

The present invention relates to surgical instruments, surgical port assemblies, and an associated method. The instruments, port assemblies and method are particularly useful in the performance of laparoscopic procedures entirely through the umbilicus.

BACKGROUND OF THE INVENTION

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through (one of) the trocar sleeve(s). Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. However, instruments used for mini-laparoscopic procedures are generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedure. In addition, smaller, 2-3 mm, incisions may still cause undesirable cosmetic outcomes and wound complications (bleeding, infection, pain, keloid formation, etc.).

Since the benefits of smaller and fewer body cavity incisions are proven, it would be attractive to perform an operation utilizing only a single incision in the navel. An umbilicus is the thinnest and least vascularized, and a well-hidden, area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. The placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems, which allow laparoscopic procedures to be performed entirely through the umbilicus while at the same time reducing or eliminating the "chopstick effect". A laparoscopic procedure performed entirely through the umbilicus, using the laparoscopic instruments and trocar system according to an embodiment of the present invention, allows one to accomplish the necessary diagnostic and therapeutic tasks while further minimizing abdominal wall trauma and improving cosmesis.

OBJECTS OF THE INVENTION

The present invention provides instruments and cannula or port assemblies for the performance of surgical procedures, particularly including laparoscopic procedures, for instance, entirely through the umbilicus.

An object of the present invention is to provide an improved port assembly for facilitating access to internal organs of a patient during laparoscopic procedures.

Another object of the present invention is to provide such a port assembly that provides enlarged workspace for the hands of the surgeon(s) when plural laparoscopic instruments are placed through the umbilicus.

An additional object of the present invention is to provide improved laparoscopic instruments for facilitating operations through the umbilicus.

These and other objects of the invention will be apparent from the drawings and descriptions herein. Although each object of the invention is believed to be attained by at least one embodiment of the invention, there is not necessarily any single embodiment that achieves all of the objects of the invention.

SUMMARY OF THE INVENTION

The present invention facilitates the performance of laparoscopic surgical procedures wherein several laparoscopic instruments are inserted into a patient through respective cannulas all extending through the same opening in the patient, for instance, through the umbilicus. The advantages of such an operation include minimizing trauma to the patient and accelerating the patient recovery.

A surgical port assembly that facilitates the performance of such a laparoscopic surgical procedure comprises, in accordance with the present invention, a cannula unit including at least one cannula member, and a holder disposable in an opening in a patient's skin for receiving the cannula component so that the cannula component is movable relative to the holder during a surgical procedure. Preferably, the cannula unit is rotatable with respect to the holder about a longitudinal axis of the holder. It is contemplated that the holder is fastened to the patient during the surgical operation, so that the cannula unit is movable relative to the patient.

Pursuant to another feature of the present invention, the cannula unit comprises a base or frame that is removably attachable to the holder and that defines a closure surface extending, during the surgical procedure, substantially tangentially to the patient's skin at the opening. The cannula member is connected to the base and defines an access path through the closure surface. The cannula member extends at an acute angle relative to the closure surface so that the cannula is inclined relative to the patient's skin surface during the surgical procedure.

Pursuant to further features of the present invention, the cannula is flexible and has a relaxed configuration that is linear. The base or frame is provided with a panel or wall forming the closure surface.

In a particular embodiment of the present invention, the cannula is one of a plurality of cannulas each extending at an acute angle relative to the closure surface so that the cannulas are all inclined relative to the patient's skin surface during the surgical procedure.

Pursuant to additional features of the present invention, the cannula unit is partially insertable into the holder, while the port assembly further comprises a connector member for removably attaching the cannula unit to the holder, the connector also being partially insertable into the holder.

The holder and the connector member may be provided with cooperating locking elements such as projections and slots for reversibly securing the cannula unit to the holder. Thus, after placement of the holder in an opening in the patient (and after removal of an insert assist member from the holder), the base or frame of the cannula unit is inserted into the holder and secured thereto by an insertion and a rotation of the connector so that the projections and slots are interlocked.

The base or frame of the cannula unit may include a frustoconical portion insertable into the holder. Similarly, the connector may include a frustoconical portion insertable into the holder to secure the cannula unit to the holder. The holder is provided internally with a shoulder engaging a lower end of the cannula unit.

As indicated above, in one embodiment of the present invention, a surgical port assembly comprises (a) a base or frame seatable in an opening in a patient's skin and defining a closure surface extending substantially tangentially to the patient's skin at the opening during a surgical procedure and (b) a cannula connected to the base and defining an access path through the closure surface. The cannula extends at an acute angle relative to the closure surface so that the cannula is inclined relative to the patient's skin surface during the surgical procedure. The cannula may be one of a plurality of cannulas each extending at an acute angle relative to the closure surface so that the cannulas are all inclined relative to the patient's skin surface during the laparoscopic procedure.

Where the closure surface is located in a main plane, the cannulas have linear configurations, and the base or frame has a longitudinal axis, each of the cannulas may define a respective secondary plane oriented perpendicularly to the main plane, each the secondary plane being spaced from the longitudinal axis. The cannulas may be three in number with the secondary planes disposed at angles of 120° relative to each other.

A surgical method in accordance with the present invention comprises forming an opening in a patient, inserting a cannula holder through the opening, disposing a plurality of cannulas in the holder so that after inserting of the holder the cannulas traverse the holder and extend from outside the patient to inside the patient, thereafter inserting a plurality of elongate medical instruments through the respective cannulas, and rotating the cannulas and the instruments relative to the holder, about a longitudinal axis of the holder.

In accordance with another aspect of the present invention, where the cannulas are attached to a base member, the disposing of the cannulas in the holder includes inserting the base member into the holder, the base member being in rotatable engagement with the holder. The disposing of the cannulas in the holder may further include attaching a locking member to the holder to maintain the base member in rotatable engagement with the holder.

A laparoscopic medical instrument insertable through a laparoscopic trocar sleeve comprises, in accordance with the present invention, an elongate shaft, an operative tip disposed at one end of the shaft, and a first actuator disposed at an opposite end of the shaft. The actuator is operatively connected to the operative tip via the shaft for controlling the operation of the operative tip. The shaft has a straight proximal end portion, a curved middle portion and a straight distal end portion, the distal end portion extending at an angle with respect to the proximal end portion. The proximal end portion is provided with a first rotary joint so that the distal end portion and the operative tip are rotatable about a longitudinal axis of the proximal end portion. The distal end portion is provided with a second rotary joint so that the operative tip is rotatable about a longitudinal axis of the distal end portion. A second actuator disposed at the end of the shaft opposite the operative tip is operatively connected to the proximal end portion of the instrument shaft for rotating the distal end portion thereof and the operative tip about the longitudinal axis of the proximal end portion of the shaft. A third actuator disposed at the end of the shaft opposite the operative tip is operatively connected to the distal end portion of the shaft for rotating the operative tip about the longitudinal axis of the distal end portion.

The proximal end portion, the middle portion and the distal end portion of the instrument shaft are each substantially rigid throughout so that they cannot be bent. In one embodiment of the invention, the instrument shaft has a hockey-stick shape. Two laparoscopic surgical instruments each having a hockey stick shape are advantageously used in a crossed configuration, which markedly improves the degrees of freedom of the instruments, particularly during lateral (medial-lateral) movements.

BRIEF DESCRIPTION OF THE DRAWINGS

FIG. 8 is a perspective view of the laparoscopic port or cannula assembly of FIGS. 1-3, together with the port holder of FIGS. 4-7, showing the laparoscopic port or cannula assembly inserted into and attached to the port holder.

FIG. 9 is a top plan view of the laparoscopic port or cannula assembly of FIGS. 1-3 connected to the port holder of FIGS. 4-7, as shown in FIG. 8.

FIG. 10 is a longitudinal cross-sectional view taken along line X-X in FIG. 9.

DETAILED DESCRIPTION OF THE PREFERRED EMBODIMENTS

Figure 1:
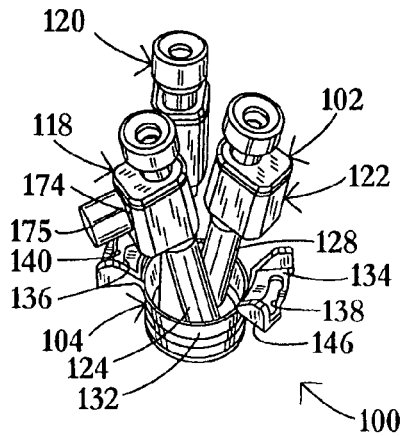
FIG. 1 is a perspective view of a laparoscopic port having multiple cannulas, in accordance with the present invention.
Figure 2:
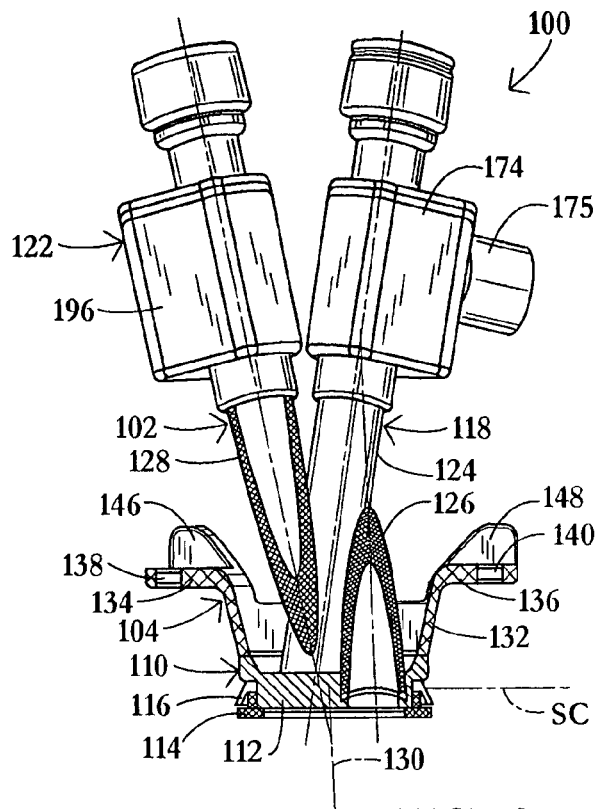
FIG. 2 is a cross-sectional view of the laparoscopic port or cannula assembly of FIG. 1, taken along line II-II in FIG. 3.
Figure 3:
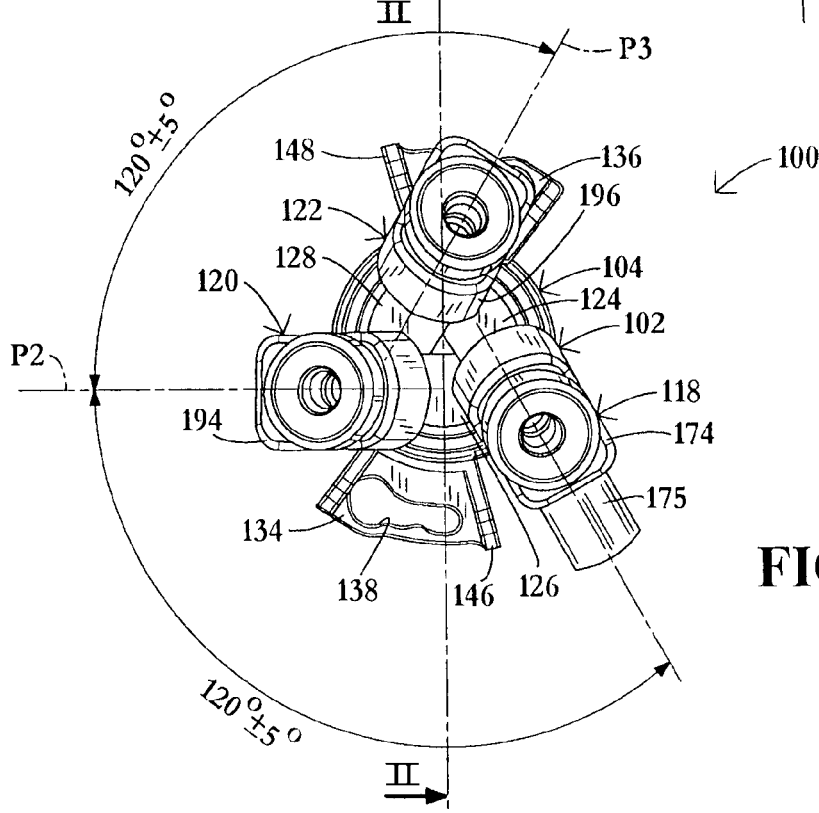
FIG. 3 is a top view of the laparoscopic port or cannula assembly of FIG. 1.
Figure 4:
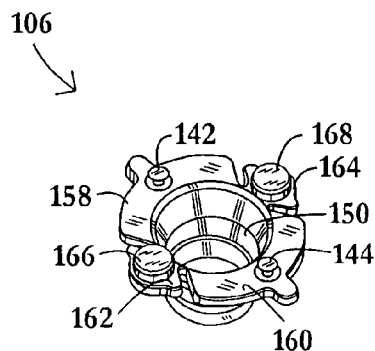
FIG. 4 is a perspective view of an annular holder disposable in an opening in a patient for receiving the laparoscopic port or cannula assembly of FIGS. 1-3.
Figure 5:
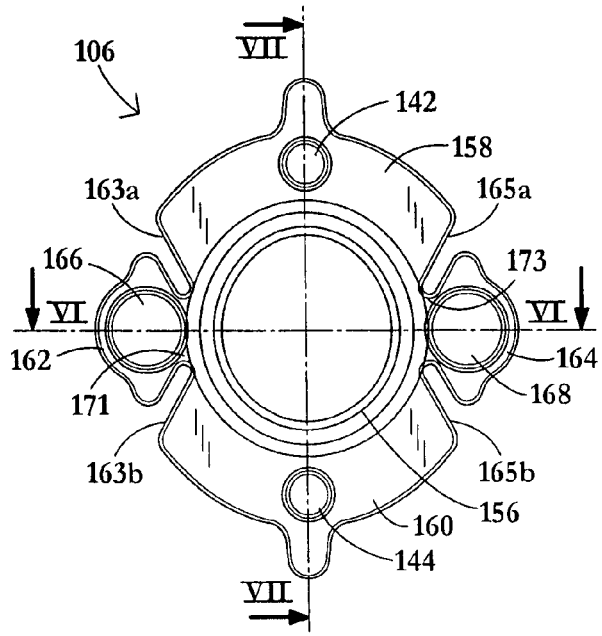
FIG. 5 is a top plan view of the port holder of FIG. 4.
Figure 6:
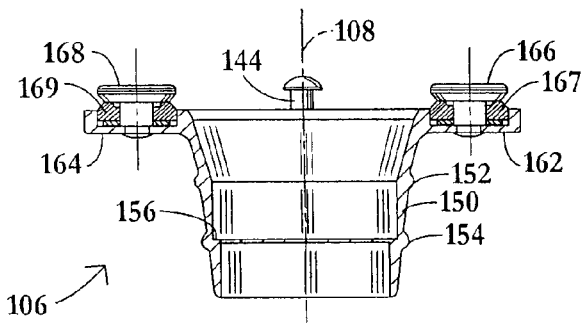
FIG. 6 is a longitudinal cross-sectional view of the port holder of FIGS. 4 and 5, taken along line VI-VI in FIG. 5.
Figure 7:
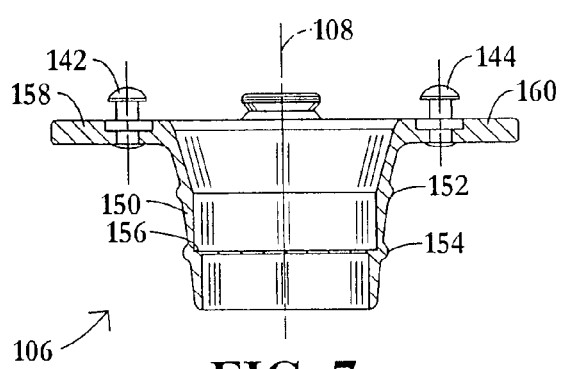
FIG. 7 is another longitudinal cross-sectional view of the port holder of FIGS. 4 and 5, taken along line VII-VII in FIG. 5.
Figure 11:
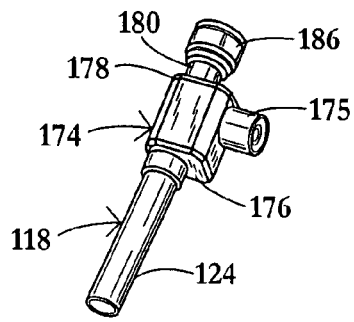
FIG. 11 is a perspective view of a cannula with an insufflation valve, included in the laparoscopic port or cannula assembly of FIGS. 1-3 and 8-10.
Figure 12:
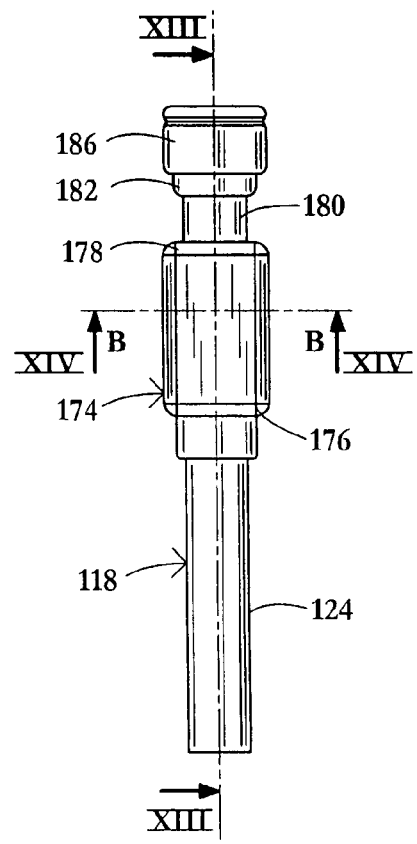
FIG. 12 is a side elevational view of the cannula of FIG. 11, on a larger scale.
Figure 13:
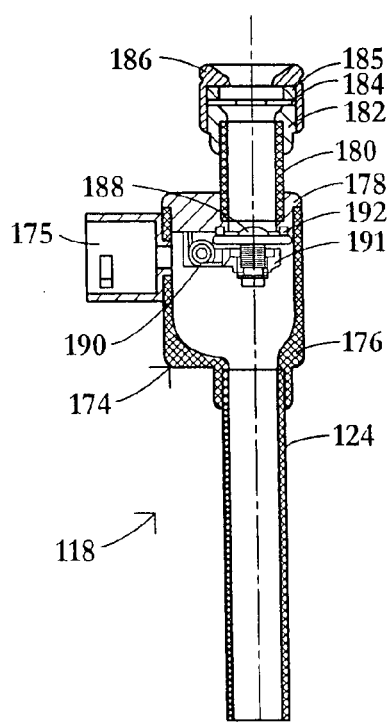
FIG. 13 is a longitudinal cross-sectional view of the cannula of FIGS. 11 and 12, taken along line XIII-XIII in FIG. 12.
Figure 14:
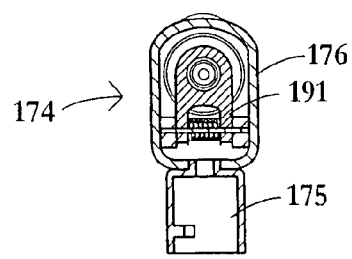
FIG. 14 is a transverse cross-sectional view of the cannula of FIGS. 11 and 12, taken along line XIV-XIV in FIG. 12.
Figure 15:
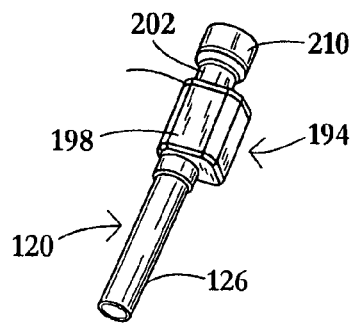
FIG. 15 is a perspective view of a cannula without an insufflation valve, included in the laparoscopic port or cannula assembly of FIGS. 1-3 and 8-10.
Figure 16:
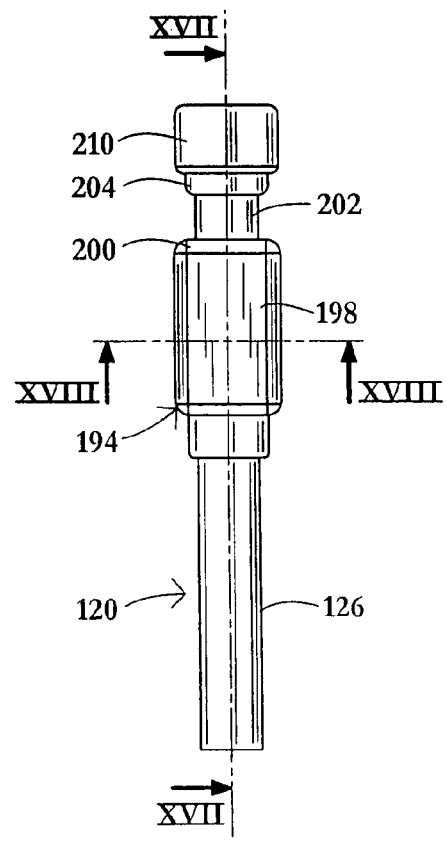
FIG. 16 is a side elevational view of the cannula of FIG. 16, on a larger scale.

As depicted in FIGS. 1-3, a laparoscopic port or cannula assembly 100 comprises a cannula unit 102 and a connector 104 associated therewith for removably fastening the cannula unit to an annular port holder 106 (FIGS. 4-8 and 10) that is disposed in an opening (e.g., formed in the umbilicus) in a patient. Cannula unit 102 is coupled to port holder 106 by connector 104 so as to permit rotation of cannula unit 102 about a longitudinal axis 108 (FIGS. 7 and 10) of holder 106. Holder 106 has an inner side facing inside the patient and an outer side facing outside the patient during a laparoscopic procedure, and axis 108 traverses the holder from the inner side to the outer side thereof.

Cannula unit 102 comprises a base or frame 110 that is insertable into and removably attachable to port holder 106. Base or frame 110 includes a base member in the form of a planar panel or wall 112 that defines a closure surface or plane SC extending, during a laparoscopic surgical procedure, substantially tangentially and accordingly parallel to the patient's skin at the opening through with port holder 106 extends. Base or frame 110 further includes a seating ring 114 and a sealing ring 116.

Cannula unit 102 additionally comprises three cannula members 118, 120, 122 each connected to base or frame 110 and defining a respective access path through closure surface SC. Cannula members 118, 120, 122 are each connected at one end to base 110 and particularly panel or wall 112 at mutually spaced locations so as to enable simultaneous insertion of multiple instruments through closure surface SC at such locations, the cannulas each extending away from closure surface SC so as to be located on only an outer side thereof opposite the patient during a surgical procedure. Cannula members 118, 120, 112 have outer surfaces (not separately designated) that are contiguous with, and stationary with respect to, planar panel or wall 112 at points of passage of the cannulas through the panel or wall. When cannula unit 102 and holder 106 are connected together (see FIG. 10), cannula members 118, 120, 122 extend into and are partially surrounded by said holder 106 and enable disposition of distal ends of three separate instruments in the patient at an opening or incision in the patient. Cannula members 118, 120, 122 each extend at an acute angle relative to closure surface SC so that the cannulas are inclined relative to the patient's skin surface during a laparoscopic surgical procedure. Cannula members 118, 120, 122 include flexible tubular portions 124, 126, 128 that have linear configurations in a relaxed or unstressed condition.

Each cannula member 118, 120, 122 defines a respective plane P1, P2, P3 (FIG. 3) oriented perpendicularly to closure surface or plane SC (the main plane) and spaced from a longitudinal axis 130 of base or frame 110. These secondary planes P1, P2, and P3 are disposed at angles of 120° relative to each other, as indicated in FIG. 3. Connector 104 is loosely coupled to cannula unit 102 so as to be freely movable along axis 130 of the cannula unit, between base 110 and valve components of cannulas 118, 120, 122.

Connector 104 includes a frustoconical portion 132 insertable into port holder 106 (see FIG. 10) and further includes a pair of flanges 134, 136 for temporarily locking cannula unit 102 to holder 106. To that end, flanges 134, 136 are provided with dual-lobed slots 138, 140 for receiving respective pins or projections 142, 144 on port holder 106 (see FIGS. 4, 5, 7, 8, 9). Flanges 134 and 136 are also provided with respective pairs of upturned ears 146 and 148 functioning in part as thumb and finger rests for swiveling connector 104 about axis 108 (and 130) to reversibly secure connector 106 and concomitantly cannula unit 102 to port holder 106.

As illustrated in FIGS. 4-7, port holder 106 includes an annular peripheral wall in the form of a tapered, slightly frustoconical sleeve 150 provided along an outer surface with a pair of annular beads or ribs 152 and 154 and along an inner surface with a shoulder 156 that serves as an abutment or rest for seating ring 114 of cannula unit 102. Peripheral wall or sleeve 150 is an outermost portion of holder 106 and is in contact with tissues of said patient upon a disposition of the holder in an opening in a patient. At a wider end of sleeve 150, holder 106 includes a pair of diametrically opposed flanges 158, 160 and a pair of diametrically opposed ears 162, 164. Pins or projections 142, 144 are rigid with flanges 158, 160, while ears 162, 164 carry respective flat-headed posts 166, 168 around which sutures are wound to fasten holder 106 to the skin of the patient. Rubber gaskets 167 and 169 may be provided for clamping suture threads to posts 166 and 168. Alternatively or additionally, sutures anchoring port holder 106 to the body wall of the patient may be inserted through slots 163a, 163b and 165a, 165b and partially wrapped around bases 171 and 173 of ears 162, 164 (see FIG. 5).

After placement of holder 106 in an opening in the patient (and after removal of an insert assist member 170, FIGS. 19-22, from the holder), base or frame 110 of cannula unit 102 is inserted into holder 106 until seating ring 114 engages shoulder 15 (see FIG. 10). Cannula unit 110 is secured to holder 106 by an insertion and a subsequent rotation of connector 104 relative to holder 106, as indicated by an arrow 172 in FIGS. 8 and 9, so that projections 142, 144 and slots 138, 140 are interlocked (see FIGS. 8-10). After this locking of connector 104 to holder 106, cannula unit 102 is rotatable about axes 108 and 130 in opposition to a frictional drag force exerted by virtue of sealing ring 116.

As illustrated in FIGS. 11-14, cannula unit 118 includes valve component 174 connected to tubular portion 124. Valve component 124 includes an insufflation port 175 for receiving a tube (not shown) for guiding carbon dioxide gas from a pressurized source into the patient. As shown particularly in FIG. 13, valve component 124 of cannula member 118 includes a valve box or casing 176 with a cover or closure 178 to which an extension tube 180 is attached. At an end opposite valve casing 176, extension tube 180 is provided with a sleeve 182, a valve seal 184, a disc 185, and a cap 186. Valve component 174 further includes a valve door 188 that is biased into a closure position shown in FIG. 13 by a helical or coil spring 190. Door 188 is supported by a mounting bracket and associated hardware 191. An O-ring seal 192 is provided for inhibiting the escape of insufflation gas from a patient through extension tube 124 when a laparoscopic surgical instrument does not traverse cannula member 118.

Figure 17:
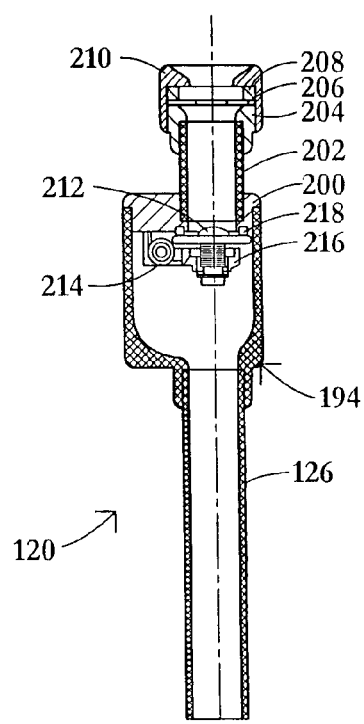
FIG. 17 is a longitudinal cross-sectional view of the cannula of FIGS. 15 and 16, taken along line XVII-XVII in FIG. 16.
Figure 18:
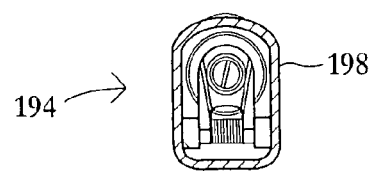
FIG. 18 is a transverse cross-sectional view of the cannula of FIGS. 15 and 16, taken along line XVIII-XVIII in FIG. 16.

As illustrated in FIGS. 1-3 and 8-10, cannula members 120 and 122 include respective valve components 194 and 196 connected to respective flexible tubular portions 126 and 128. These valve components are structurally identical, a representative component 194 being depicted in FIGS. 15-18. Valve component 194 includes a valve box or casing 198 with a cover or closure 200 to which an extension tube 202 is attached. At an end opposite valve casing 198, extension tube 202 is provided with a sleeve 204, a valve seal 206, a disc 208, and a cap 210. Valve component 194 further includes a valve door 212 that is biased into a closure position shown in FIG. 17 by a helical or coil spring 214. Door 212 is supported by a mounting bracket and associated hardware 216. An O-ring seal 218 is provided for inhibiting the escape of insufflation gas from a patient through extension tube 202 when a laparoscopic surgical instrument does not traverse the respective cannula member 120 (or 122).

Figure 19:
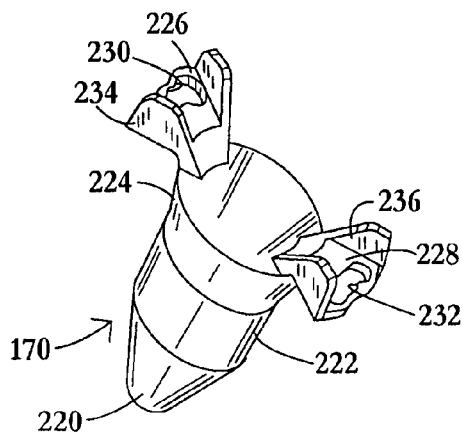
FIG. 19 is a perspective view of an insertion plug used to facilitate insertion of the port holder of FIGS. 4-7 in a patient at the beginning of a laparoscopic procedure.
Figure 20:
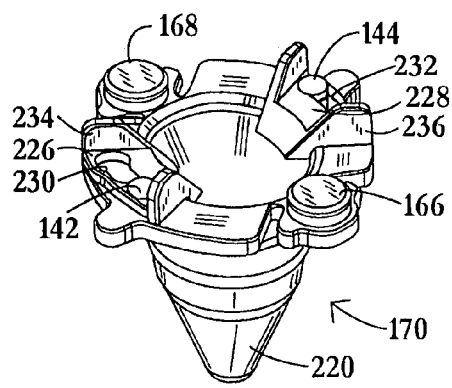
FIG. 20 is a top perspective view of the insertion plug of FIG. 19 temporarily inserted in and attached to the port holder of FIGS. 4-7.
Figure 21:
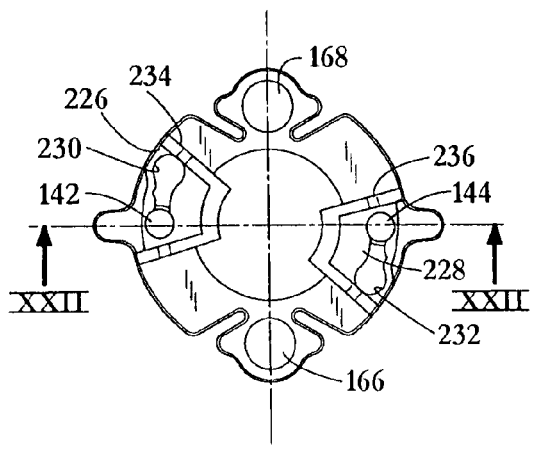
FIG. 21 is a top plan view of the assembled insertion plug and port holder of FIG. 20.
Figure 22:
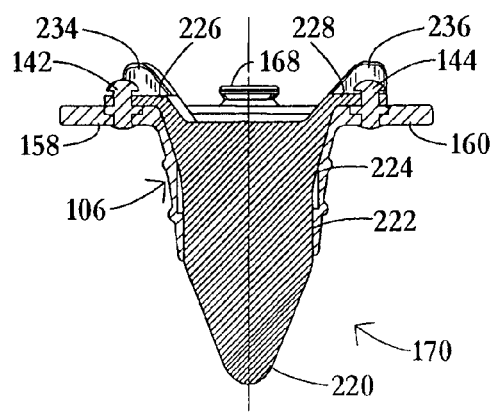
FIG. 22 is a longitudinal cross-section taken along line XXII-XXII in FIG. 21.
Figure 23:
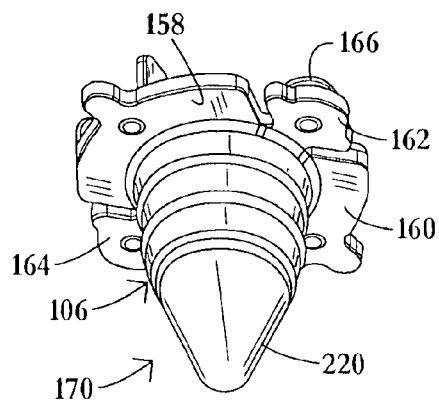
FIG. 23 is a bottom perspective view of the assembled insertion plug and port holder of FIGS. 20-22.

As shown in FIG. 19, insert assist member 170 includes a rounded conical tip 220, a cylindrical middle portion 222 and a slightly tapered or frustoconical outer portion 224. Outer portion 224 is provided with a pair of flanges 226, 228 for temporarily locking insert assist member 170 to port holder 106. To that end, flanges 226, 228 are provided with dual-lobed slots 230, 232 for receiving respective pins or projections 142, 144 on port holder 106, as depicted in FIGS. 20-22. Flanges 226 and 228 are formed with respective pairs of upturned ears 234 and 236 that are manually engageable by a user to reversibly secure connector insert assist member 170 to port holder 106.

After a small incision or opening is made in a patient, port holder 106 with insert assist member 170 connected thereto is inserted through the incision. Sutures (not shown) are stitched to the patient and are wound around and tied to posts 166, 168 to firmly secure the port holder 106 to the patient. Insert assist member 170 is then removed, by a reverse rotation unlocking flanges 226, 228 from pins or projections 142, 144 and by separating the inset assist member from holder 106. Cannula unit 102 is then attached to holder 106 as described above.

FIGS. 24-29 depict a laparoscopic surgical instrument 238 insertable through a laparoscopic trocar sleeve or cannula such as cannula member 118, 120, or 122 of the port assembly of FIGS. 1-3 and 8-10 for executing a laparoscopic surgical operation. Instrument 238 comprises an elongate shaft 240, an operative tip 242 disposed at one end of the shaft, and a hand-grip-type actuator 244 disposed at an opposite end of the shaft. Actuator 244 is operatively connected to operative tip 242 via shaft 240 for controlling the operation of the operative tip.

Figure 24:
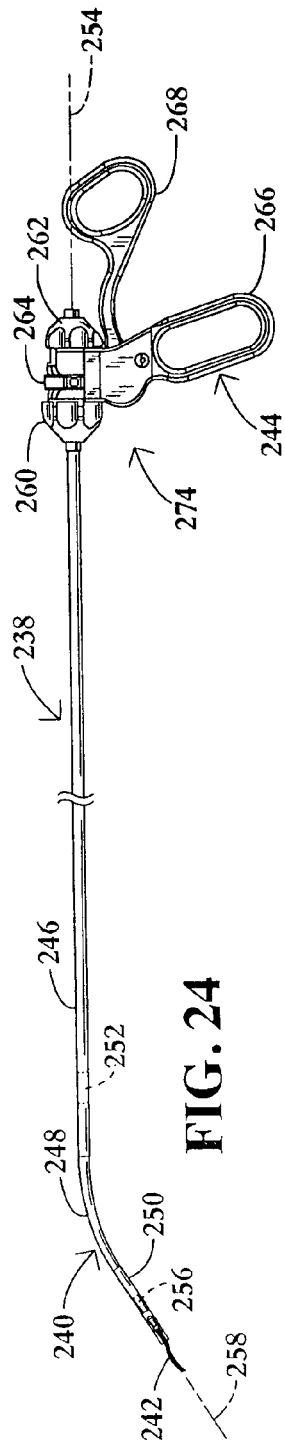
FIG. 24 is a side elevational view of a laparoscopic instrument utilizable with the multiple-cannula port assembly of FIGS. 8-10, in accordance with the present invention.
Figure 26:
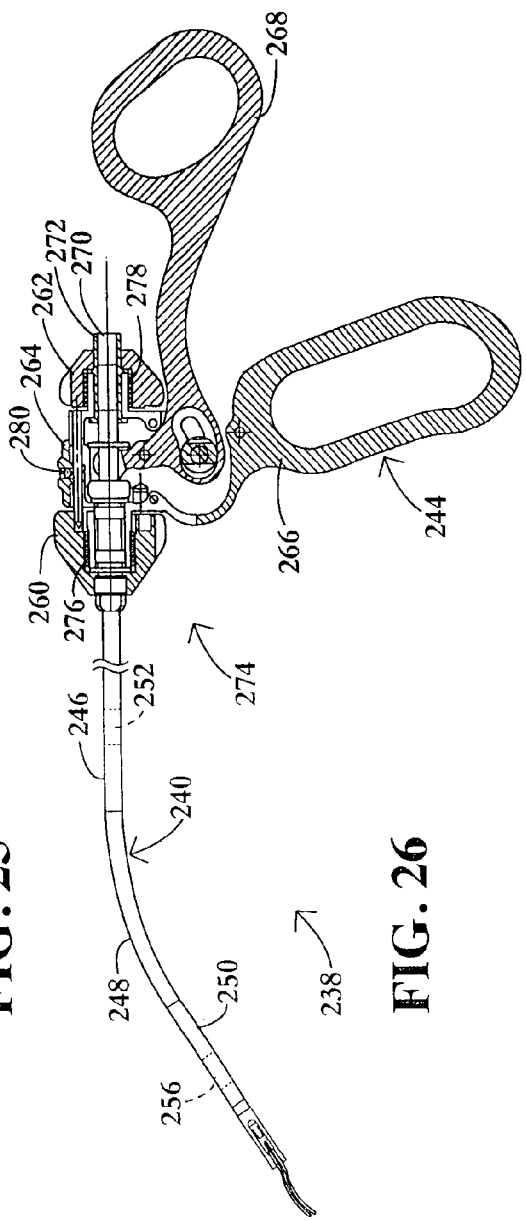
FIG. 26 is partially a side elevational view and partially a cross-sectional view taken along line XXVI-XXVI in FIG. 25.
Figures 27, 28, 29:
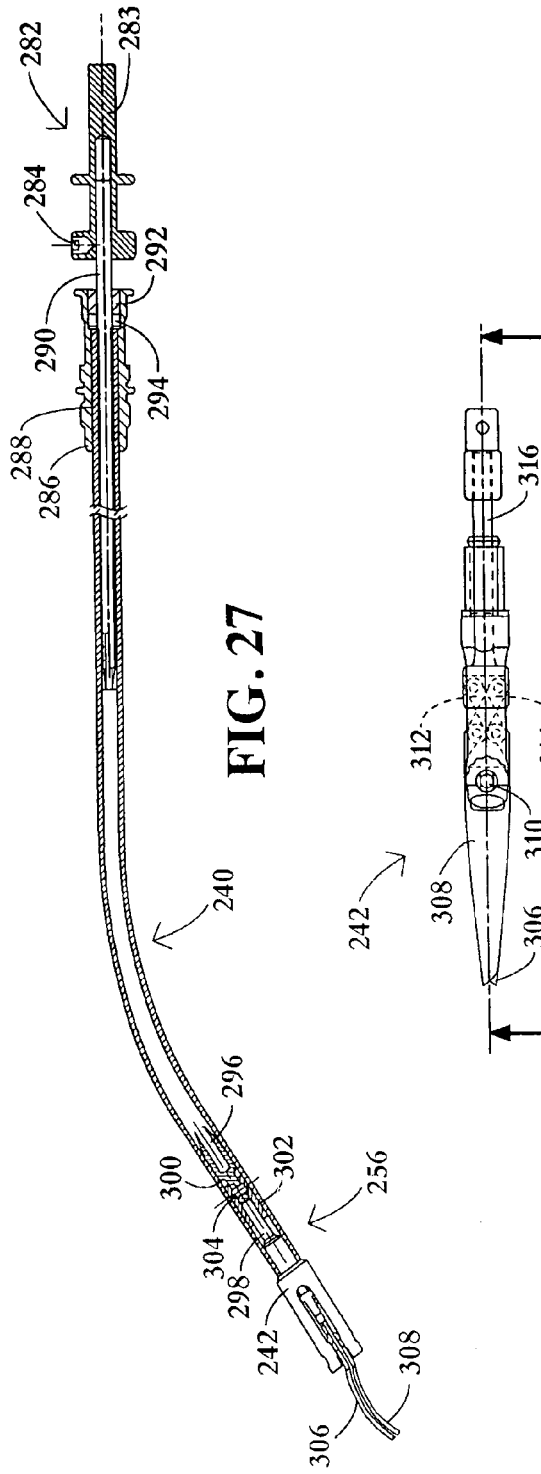
FIG. 27 is a partial longitudinal cross-sectional view also taken along line XXVI-XXVI in FIG. 25.
FIG. 28 is a longitudinal cross-sectional view, on a larger scale, of a distal end of the laparoscopic instrument of FIGS. 24-27.
FIG. 29 is a longitudinal cross-sectional view, on an even larger scale, taken along line IXXX-IXXX in FIG. 28.

Shaft 240 has a straight proximal end portion 246, a curved middle portion 248 and a straight distal end portion 250, the distal end portion extending at a non-zero angle with respect to the proximal end portion, as shown in FIGS. 24, 26 and 27. Proximal end portion 246 is provided with a first rotary joint 252 so that distal end portion 250 and operative tip 242 are rotatable about a longitudinal axis 254 of proximal end portion 246. Distal end portion 250 is provided with a second rotary joint 256 so that operative tip 242 is rotatable about a longitudinal axis 258 of the distal end portion. A rotary actuator or knob 260 disposed at the proximal end of instrument 238 is operatively connected to proximal end portion 246 of instrument 240 for rotating distal end portion 250 and operative tip 242 about longitudinal axis 254. Another rotary actuator or knob 262 disposed at the proximal end of instrument 238 is operatively connected to distal end portion 250 of shaft 240 for rotating operative tip 242 about longitudinal axis 258.

Proximal end portion 246, middle portion 248 and distal end portion 250 of instrument shaft 240 are each substantially rigid throughout and can only be rotated about joints 252 and 256 and not bent. The angle between axes 254 and 258 are such that shaft 240 has a shape reminiscent of a hockey stick. In an alternative embodiment of instrument 238, middle portion 248 of shaft 240 may be flexible to permit shaft 240 to alternately assume a linear configuration and the hockey-stick configuration of FIGS. 24 and 26. In that case, a handle assembly 274 is provided with an actuator (not shown) for enabling a bending of middle portion 248.

Figure 25:
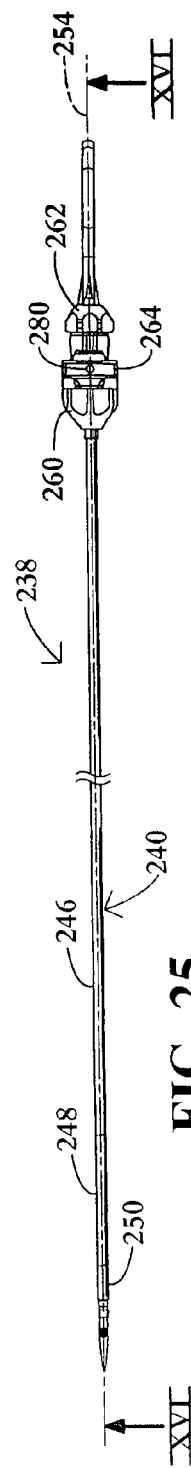
FIG. 25 is a top plan view of the laparoscopic instrument of FIG. 24.

As shown in FIGS. 24-26, instrument 238 may be provided with further actuators, such as a slidable toggle switch 264, for example for performing a locking function or inducing a pivoting of operative tip 242 about an axis perpendicular to axis 258.

Actuator 244 includes a hand grip member 266 fixed relative to shaft 240 and further includes a pivotable hand grip 268. A proximal end 270 of shaft 240 is journaled in a bearing 272 about which rotary knob 262. Actuator 244, rotary knobs 260 and 262, and toggle switch 264 are parts of a handle assembly 274 also incorporating yokes 276 and 278, a stopper pin 278, a set screw 280.

FIG. 27 illustrates further parts of a shaft assembly 282 including shaft 240, a slider member 283, a socket set screw 284, an outer bearing 286, a motion bar 288, a bend tube 290, a ring 292, and an O-ring seal 294.

Rotary joint 256 is representative of joint 254 and comprises, as shown in FIG. 27, a proximal pin or inner shaft portion 296, a distal pin or inner shaft portion 298, a pair of coupling elements 300 and 302, and a transverse connector pin 304.

As illustrated in FIGS. 28 and 29, operative tip 242 exemplarily includes a pair of jaws 306 and 308 pivotably connected to a distal end of distal end portion 250 via a pivot pin 310. Jaws 306 and 308 are rotatable about pin 310 through the action of levers or arms 312, 314 that pivot in response to a longitudinal motion of a tip rod 316.

After a deployment of cannula unit 102 in a patient as described above, operative tip 242 and shaft 240 of instrument 238 are insertable through a cannula member 118, 120, or 122, with the respective tubular portion 124, 126, or 128 bending to accommodate the bent shaft 240. The bent shape of shaft 240, as well as the rotary joints 252 and 256 facilitate the performance of laparoscopic surgical procedure using multiple laparoscopic instruments extending through a single opening in a patient, for instance, in the umbilicus. Such a procedure involves the rotation of distal end portion 250 and operative tip 242 together about axis 254 and the rotation of operative tip about axis 258. In addition, the entire instrument assembly including cannula unit 102 and multiple instruments 238 can be rotated about collinear axes 108 and 130, to optimize the simultaneous or successive access of multiple operative tips 242 to a surgical site inside a patient.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical port assembly comprising:
    an annular holder disposable in an opening in a patient, said annular holder having an annular wall or sleeve, said annular wall or sleeve being an outermost portion of said holder so that said wall or sleeve is in contact with soft tissues of said patient at said opening upon a disposition of said holder in said opening,
    said annular holder configured and dimensioned to secure directly to the soft tissues of said patient;
    a cannula unit removably attachable to said holder so that said cannula unit is rotatable with respect to said holder about a longitudinal axis, said cannula unit comprising:
    a base removably attachable to said holder so as to be disposed at least partially inside said annular wall or sleeve, said base defining a closure surface disposed inside said annular wall or sleeve so that said annular wall or sleeve surrounds said closure surface; and
    a plurality of cannulas connected to said base so as to intersect said closure surface within said annular wall or sleeve, said cannulas defining respective access paths passing through said closure surface at mutually spaced locations so as to enable simultaneous insertion of multiple instruments through said closure surface at said locations, said cannulas being separate and distinct tubular members each fixedly connected at one end to said base so that portions of said cannulas contiguous with said closure surface are stationary with respect to said closure surface,
    wherein said closure surface is located in a main plane, each of said cannulas defining a respective secondary plane to said main plane, said base having a longitudinal axis, each said secondary plane being spaced from said longitudinal axis, and
    wherein said cannulas are at least three in number and said secondary planes are disposed at angles relative to each other.

2. The port assembly defined in claim 1
    wherein said closure surface extends substantially parallel to the patient's skin at said opening during a surgical procedure; and
    wherein at least one of said cannulas extends at an acute angle relative to said closure surface so that said at least one of said cannulas is inclined relative to the patient's skin surface at least in a relaxed or rest configuration of the port assembly.

3. The port assembly defined in claim 1 wherein said at least one of said cannulas is flexible.

4. The port assembly defined in claim 2 wherein said at least one of said cannulas has a relaxed configuration that is linear.

5. The port assembly defined in claim 3 wherein said base is provided with a panel or wall forming said closure surface.

6. The port assembly defined in claim 1, further comprising a connector member for removably attaching said cannula unit to said holder, said connector also being partially insertable into said holder.

7. The port assembly defined in claim 6 wherein said holder and said connector member are provided with cooperating locking elements.

8. The port assembly defined in claim 7 wherein said locking elements include projections on one of said holder and said connector member and further include slots on the other of said holder and said connector member.

9. The port assembly defined in claim 6 wherein said connector includes a portion insertable into said holder to secure said cannula unit to said holder.

10. The port assembly defined in claim 1 said holder is provided internally with a shoulder engaging a lower end of said cannula unit.

11. The port assembly defined in claim 1 wherein said holder is provided with means for releasably securing said base member to the patient.

12. A surgical port assembly comprising:
    a base seatable in an opening in a patient's skin, said base defining a closure surface, said closure surface extending substantially parallel to the patient's skin at said opening during a surgical procedure previously presented,
    said base configured and dimensioned to secure directly to the skin of said patient; and
    a plurality of cannulas connected to said base and defining respective access paths through said closure surface, said cannulas extending at acute angles relative to said closure surface so that said cannulas are inclined relative to the patient's skin surface at least in a relaxed or rest configuration of the port assembly, said cannulas being separate and distinct tubular members each connected at one end to said base, portions of said cannulas contiguous with said closure surface being fixed to said base so as to be stationary with respect to said closure surface,
    wherein said closure surface is located in a main plane and said cannulas have linear configurations, each of said cannulas defining a respective secondary plane to said main plane, said base having a longitudinal axis, each said secondary plane being spaced from said longitudinal axis, and
    wherein said cannulas are at least three in number and said secondary planes are disposed at angles relative to each other.

13. The port assembly defined in claim 12 wherein said cannulas are flexible.

14. The port assembly defined in claim 13 wherein said cannulas each have a relaxed or unstressed configuration that is linear.

15. The port assembly defined in claim 12 wherein said base is provided with a panel or wall forming said closure surface.

16. The port assembly defined in claim 12, further comprising a connector element for removably attaching said base and said cannula to a holder so that said base and cannula are movably secured to said holder, wherein said holder is seatable in an opening in a patient during a surgical procedure.

17. A surgical port assembly comprising:
    a base seatable in an opening in a patient,
    said base configured and dimensioned to be secured by skin of said patient; and at least three separate cannula members connected to said base and defining respective access paths through the opening in the patient enabling positioning of distal ends of separate surgical instruments, said cannula members being oriented at angles relative to one another and to said base in a relaxed or rest configuration of the port assembly, wherein said cannula members are three in number and oriented at angles of 120° with respect to each other and wherein said cannula members are jointly rotatable relative to said base about an axis perpendicular to the skin of the patient.

18. The port assembly defined in claim 17, further comprising a connector element for removably attaching said base with said cannula members to a holder so that said base and cannula are movably secured to said holder, wherein said holder is seatable in an opening in a patient during a surgical procedure.

19. A surgical port assembly comprising:

an annular holder disposable in an opening in a patient, said holder having an outer side and an inner side, said annular holder configured and dimensioned to secure directly to skin of said patient;

at least three cannulas; and structure coupling said cannulas to said holder so that said cannulas enable disposition of distal ends of separate instruments in the patient at the opening in the patient, so that said cannulas extend into and are partially surrounded by said holder, and so that said at least three cannulas are jointly rotatable relative to said holder about an axis traversing said holder from said outer side to said inner side, said structure including a base member disposed inside said holder so that said holder surrounds said base member, said cannulas being separate and distinct tubular members connected at respective ends to said base member at mutually spaced locations so as to enable simultaneous insertion of multiple instruments through said base member at said locations, outer surfaces of said cannulas being contiguous with and fixed to said base member so as to be stationary with respect to said base member at points of passage of said cannulas through said base member, wherein said cannulas are oriented at angles with respect to each other.

20. The surgical port assembly defined in claim 19 wherein said holder has an annular wall or sleeve and wherein said structure coupling said cannulas to said holder includes a base removably attachable to said holder so as to be disposed at least partially inside said annular wall or sleeve, said base defining a closure surface disposed inside said annular wall or sleeve so that said annular wall or sleeve surrounds said closure surface, said cannulas being connected to said base so as to intersect said closure surface within said annular wall or sleeve, said cannula defining respective access paths through said closure surface.

21. The port assembly defined in claim 20 wherein said cannulas extend at acute angles relative to said closure surface so that said cannulas are inclined relative to the patient's skin surface at least in a relaxed or rest configuration of the cannulas.

22. The port assembly defined in claim 19 wherein said structure coupling said cannulas to said holder includes a connector member for removably attaching said cannulas to said holder, said connector being partially insertable into said holder.

23. The port assembly defined in claim 22 wherein said holder and said connector member are provided with cooperating locking elements.

24. A surgical port assembly comprising: a base seatable in an opening in a patient, said base configured and dimensioned to be secured by skin of said patient; and at least three separate cannula members connected to said base and defining respective access paths through the opening in the patient enabling positioning of distal ends of separate surgical instruments, said cannula members being oriented at angles relative to one another and to said base in a relaxed or rest configuration of the port assembly, wherein said cannula members are three in number and oriented at fixed angles of about 120° with respect to each other and wherein said cannula members are jointly rotatable relative to said base.

* * * * *